US007601346B1

(12) United States Patent
Schisler et al.

(10) Patent No.: US 7,601,346 B1
(45) Date of Patent: Oct. 13, 2009

(54) CHOLINE-UTILIZING MICROBIAL STRAINS FOR BIOLOGICALLY CONTROLLING FUSARIUM HEAD BLIGHT

(75) Inventors: David A. Schisler, Morton, IL (US); Naseem I. Khan, Peoria, IL (US); Michael J. Boehm, Worthington, OH (US); Patricia J. Slininger, Metamora, IL (US)

(73) Assignees: The United States of America, as represented by the Secretary of Agriculture, Washington, DC (US); The Ohio State University Research Foundation, Columbus, OH (US)

( * ) Notice: Subject to any disclaimer, the term of this patent is extended or adjusted under 35 U.S.C. 154(b) by 0 days.

(21) Appl. No.: 11/640,091

(22) Filed: Dec. 15, 2006

Related U.S. Application Data

(60) Provisional application No. 60/754,444, filed on Dec. 28, 2005.

(51) Int. Cl.
*A01N 63/00* (2006.01)

(52) U.S. Cl. ................ 424/93.4; 435/254.1; 435/252.1; 435/252.4; 424/93.46; 424/93.5

(58) Field of Classification Search ....................... None
See application file for complete search history.

(56) References Cited

OTHER PUBLICATIONS

Li & Ljungdahl, Applied & Environmental Microbiology, 1994, vol. 60. No. 9, p. 3160-3166.*
Duffy et al., Annu. Rev. Phytopathol 2003, vol. 41, p. 501-538.*
Schisler et al., Plant disease, 2002, vol. 86, No. 12, p. 1350-1356.*
Khan et al., Plant disease, 2001, vol. 85, No. 12, p. 1253-1258.*
Engle et al., Plant Disease, Feb. 2004, vol. 88, No. 2, p. 175-180.*
Meskeys et al., Eur. J. Biochem. 2001, vol. 268, p. 3390-3398.*
Fokkema & Meulen (Neth. J. Pl. Path, 1976, vol. 82, p. 13-16).*

* cited by examiner

*Primary Examiner*—L Blaine Lankford
*Assistant Examiner*—Kade Ariani
(74) *Attorney, Agent, or Firm*—John D. Fado; Randall E. Deck; Lesley Shaw

(57) ABSTRACT

Three choline utilizing strains of microorganisms isolated from the anthers of wheat, *Aureobasidium pullulans* strain AS 55.2, *Arthrobacter* species strain OH 221.3, and *Pseudomonas* species strain AS 64.4, are superior antagonists of *F. graminearum*. These microorganisms are effective for suppression and control of FHB in cereals, particularly in wheat and barley.

20 Claims, 2 Drawing Sheets

CHOLINE-UTILIZING MICROBIAL STRAINS FOR BIOLOGICALLY CONTROLLING FUSARIUM HEAD BLIGHT

CROSS-REFERENCE TO RELATED DOCUMENTS

This application claims the benefit under 35 U.S.C. 1.19(e) of U.S. provisional patent application No. 60/754,444, filed Dec. 28, 2005, the contents of which are incorporated by reference herein.

BACKGROUND OF THE INVENTION

1. Field of the Invention

The invention is drawn to novel biocontrol agents for control of *Fusarium* head blight.

2. Description of the Prior Art

*Fusarium* head blight (FHB) is a devastating disease of wheat and barley throughout the semi-humid and humid cereal producing regions of the world (McMullen et al., 1997; Muthomi et al., 2002; Yu. Gagkaeva and Yli-Mattila, 2004). FHB is caused primarily by *Fusarium graminearum* Schwabe Group 2 (Aoki and O'Donnell, 1999) (perfect state=*Gibberella zeae* (Schwein.) Petch). In addition to causing grain yield loss, *G. zeae* can produce mycotoxins such as the estrogenic toxin zearalenone (F-2) (Hesseltine et al., 1978) and the trichothecene deoxynivalenol (DON, vomitoxin) (Snijders, 1990) that can have a deleterious effect on grain quality (Cardwell et al., 2001) and animal health (Marasas, 1991; Beardall and Miller, 1994; Pestka and Bondy, 1994).

Reducing the impact of FHB on grain production and quality remains an intractable problem. Fungicides sometimes have reduced FHB (Wilcoxson, 1996; Suty and Mauler-Machnik, 1997; Jones, 1999), but residues, reports of fungicide resistance and instances of DON content increases in grain can be concerns with their use (Mauler-Machnik and Zahn, 1994; Ramirez et al., 2004; Chen et al., 2000; Gale et al., 2002). Although the development of resistant cultivars or anatomically altered varieties (Legzdina and Buerstmayr, 2004) of small grains holds promise in reducing FHB, highly resistant cultivars with ideal agronomic traits have not been developed (Johnston, 1994; Bushnell et al., 1998; Bai et al., 2000). The genetic diversity of *G. zeae* (O'Donnell et al., 2004, McCallum et al., 2004; Walker et al., 2001; Cumagun et al., 2004) raises concerns regarding how durable the efficacy of fungicides and resistant cultivars will be. Conventional tillage of fields is partially effective in reducing pathogen inoculum production and, concomitantly, FHB (Miller et al., 1998; Dill-Macky and Jones, 2000; Pereyra et al., 2004), but minimum tillage is the preferred agricultural practice for soil conservation. Considering the potential of long distance inoculum dispersal and the diverse crops that can act as alternative hosts of the pathogen (Chongo et al., 2001), crop rotation is an untenable solution.

Biological control of FHB has attracted considerable interest since the mid 1990's, and significant advances have been achieved (Perondi et al., 1996; Bujold et al., 2001, Schisler et al., 2002b; da Luz et al., 2003; Gilbert & Fernando, 2004). Public acceptance, compatibility with other disease management measures, and durability are all favorable factors in support of developing strategies for biologically controlling FHB.

However, despite these and other advances, the need remains for improved microorganisms for use in the biological control of FHB.

SUMMARY OF THE INVENTION

We have now discovered three microorganisms which are superior antagonists of *F. graminearum*. These microorganisms are effective for suppression and control of FHB in cereals, particularly in wheat and barley. The three microorganisms are *Aureobasidium pullulans* strain AS 55.2, *Arthrobacter* species strain OH 221.3, and *Pseudomonas* species strain AS 64.4.

The antagonists were selected from a pool of more than 700 microbial strains obtained from anthers of wheat. Initial selection of specific anther colonists for further study was based on the ability of a colonist to utilize choline. Selected microbes were then bioassayed on seed heads of a cereal plant, inoculated with *F. graminearum*, for the ability of the strain to reduce the severity of FHB. The three antagonists selected in this manner were superior in reducing FHB severity in greenhouse and in field trials.

In accordance with this discovery, it is an object of this invention to provide novel microbial strains that suppress the profusion of *F. graminearum* in heads of wheat and barley.

This and other objects of the invention will become readily apparent from the ensuing description.

DETAILED DESCRIPTION OF THE INVENTION

Figure 1:
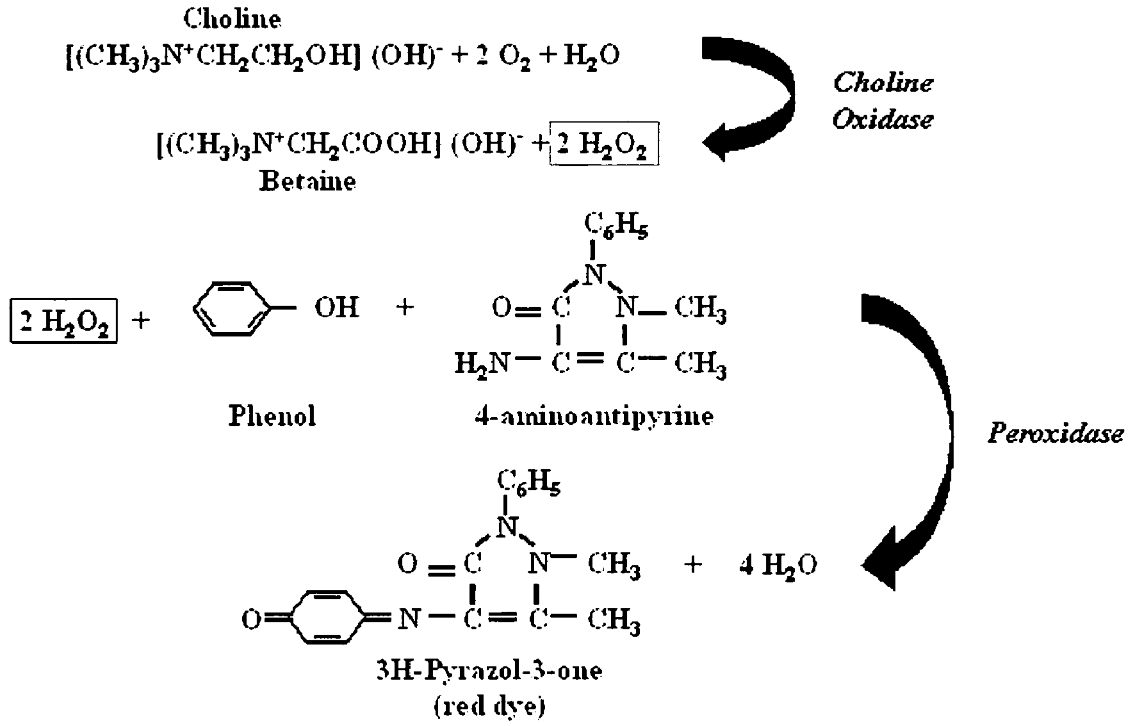
FIG. 1 shows a reaction scheme for the enzymatic determination of the presence of choline in microbial culture broths.

For purposes of this invention it is understood that the use of term *Fusarium* is intended to include both the sexual (teleomorphic) stage of this organism and also the asexual (anamorphic) stage, also referred to as the perfect and imperfect fungal stages, respectively. For example, the anamorphic stage of *Gibberella zeae* is known as *Fusarium graminearum*, the causative agent of FHB. This disease results when the flower or head (also known as seed head) becomes inoculated with conidia produced by the imperfect form OR ascospores produced by the perfect form of this fungus with infection of the inoculated head ensuing after the inoculation event.

The expression "superior antagonist" used herein in reference to a microorganism is intended to mean that the subject strain exhibits a degree of inhibition of *Fusarium*-induced head blight exceeding, at a statistically significant level, that of an untreated control.

The term cereal as used herein is intended to refer to any cereal species that is normally susceptible to FHB. Cereals reported to be susceptible include wheat, barley, oats, and triticale, though wheat and barley are the two crops in which this disease presents a significant economic problem. Tests in the Examples, below, with one variety of hard red spring wheat and two varieties of soft red winter wheat demonstrate that antagonist strains of this invention are efficacious in reducing FHB on all these types and varieties of wheat. Any of these cereals may be target species for FHB control.

The three microorganisms of this invention, *Aureobasidium pullulans* strain AS 55.2, *Arthrobacter* species strain OH 221.3, and *Pseudomonas* species strain AS 64.4, are all choline utilizing strains isolated in pure form from the anthers of wheat. Choline and betaine are found in wheat flower parts and are especially concentrated in wheat anthers. These compounds have been implicated in stimulating hyphal growth of *Gibberella zeae* and may enhance the ability of the pathogen to incite *Fusarium* head blight. It is therefore believed that the microorganisms of this invention provide protection from *Gibberella zeae* infection by metabolizing choline, thereby functioning as antagonists or competitors of the pathogen.

The isolated choline utilizing strains of this invention were identified as members of the genera *Pseudomonas* and *Arthrobacter* and as *Aureobasidium pullulans* (Table 2) by MIDI Labs (Newark, Del.) using 16S or large subunit rDNA gene sequence homologies with known strains as determined by Applied Biosystems MicroSeq™ microbial analysis software and database (Foster City, Calif.). The isolated *Pseudomonas* and *Arthrobacter* strains exhibit morphological, cultural, and biochemical properties characteristic of *Pseudomonas* and *Arthrobacter* species as described in Bergey's Manual of Determinative Bacteriology (Holt et al., 1994), the contents of which are incorporated by reference herein. The isolated *Aureobasidium* strain exhibits morphological and cultural properties characteristic of *Aureobasidium pullulans* as described by G. S. de Hoog et al. (Atlas of Clinical Fungi, Centraalbureau voor Schimmelcultures, Utrecht, The Netherlands, 2000), the contents of which are also incorporated by reference herein. The three choline utilizing isolates of this invention, *Aureobasidium pullulans* strain AS 55.2, *Arthrobacter* species strain OH 221.3, and *Pseudomonas* species strain AS 64.4, have been deposited on Jun. 8, 2009 under the provisions of the Budapest Treaty in the Agricultural Research Service Culture Collection (NRRL), 1815 N. University St., Peoria, IL, 61604, USA, and have been assigned Deposit Accession Nos. NRRL Y-50291, NRRL B-50290, and NRRL B-50289, respectively.

As described in greater detail hereinbelow, control of FHB may be effected by application of one or more of *Aureobasidium pullulans* strain AS 55.2, *Arthrobacter* species strain OH 221.3, and *Pseudomonas* species strain AS 64.4 to the head (also referred to as seed head) of a cereal plant. As used herein, the "head" or "seed head" refers to the spike that contains seeds or the progenitors of seeds. The antagonists are applied in an amount effective to reduce the level of *Fusarium* head blight relative to that in an untreated control.

Although the above-mentioned antagonists are effective when used alone, in an optional yet preferred embodiment, they are applied in combination with other known biological control agents for FHB. A variety of other biological control agents are suitable for use herein and include but are not limited to those disclosed by Perondi et al., 1996; Bujold et al., 2001, Schisler et al., 2002b; da Luz et al., 2003; Gilbert & Fernando, 2004, and Schisler et al., U.S. Pat. Nos. 6,562,337 and 6,312,940, the contents of all of which are incorporated by reference herein. Use in combination with the microbial antagonists disclosed in the Schisler patents is preferred, specifically *Bacillus* sp. (NRRL B-30210), *Bacillus* sp. (NRRL B-30211), *Torula aurea* (recently renamed *Cryptococcus aureus*) (NRRL Y-30213), an unidentified yeast (NRRL Y-30214), *Bacillus* sp. (NRRL B-30212), *Torula* sp. (recently renamed *Cryptococcus aureus*) (NRRL Y-30215), and *Cryptococcus nodaensis* (recently renamed *C. flavescens*) (NRRL Y-30216), with *Cryptococcus nodaensis* (NRRL Y-30216) being particularly preferred. These additional antagonists may be applied with the antagonists of the invention, such as in a mixture, or they may be applied separately or at different times.

Optimal conditions for the cultivation of antagonists of this invention will, of course, depend upon the particular strain. However, by virtue of the conditions applied in the selection process and general requirements of most microorganisms, a person of ordinary skill in the art would be able to determine essential nutrients and conditions.

The antagonists would typically be grown in aerobic liquid cultures on media which contain sources of carbon, nitrogen, and inorganic salts that can be assimilated by the microorganism and supportive of efficient cell growth. Preferred carbon sources are hexoses such as glucose, but other sources that are readily assimilated such as amino acids, may be substituted. Many inorganic and proteinaceous materials may be used as nitrogen sources in the growth process. Preferred nitrogen sources are amino acids and urea but others include gaseous ammonia, inorganic salts of nitrate and ammonium, vitamins, purines, pyrimidines, yeast extract, beef extract, proteose peptone, soybean meal, hydrolysates of casein, distiller's solubles, and the like. Among the inorganic minerals that can be incorporated into the nutrient medium are the customary salts capable of yielding calcium, zinc, iron, manganese, magnesium, copper, cobalt, potassium, sodium, molybdate, phosphate, sulfate, chloride, borate, and like ions. Without being limited thereto, use of semidefined liquid medium, SDCL, of Slininger et al. (1994) is preferred.

For the organisms of the invention, cell growth can be achieved at temperatures between 1 and 36° C., with the preferred temperature being in the range of 15-30° C. The pH of the nutrient medium can vary between 4 and 9, but the preferred operating range is pH 6-8. Ordinarily, maximal cell yield is obtained in 20-72 hours after inoculation.

The antagonists of the invention can be applied by any conventional method to the surfaces of cereal heads. For example, they can be applied as an aqueous spray or dip, as a wettable powder, or as a dust. However, when preparing dried formulations, rapid drying may decrease efficacy and should be avoided, particularly when formulating the above-mentioned *Pseudomonas* sp. strain. Formulations designed for these modes of application will usually include a suitable liquid or solid carrier together with other adjuvants, such as wetting agents, sticking agents and the like. Starch, polysaccharides, sodium alginate, cellulose, etc. are often used in such formulations as carriers and sticking agents.

The expressions "an effective amount" and "a suppressive amount" are used herein in reference to that quantity of antagonist treatment which is necessary to obtain a reduction in the level of disease relative to that occurring in an untreated control under suitable conditions of treatment as described herein. The actual rate of application of a liquid formulation will usually vary from a minimum of about $1\times10^3$ to about $1\times10^{10}$ viable cells/ml and preferably from about $1\times10^6$ to about $5\times10^9$ viable cells/ml. Under most conditions, the strains of the invention described in the examples, below, would be optimally effective at application rates in the range of about $1\times10^6$ to $1\times10^9$ viable cells/ml for the *Aureobasidium*, and about $1\times10^6$ to $1\times10^9$ viable cells/ml for the *Arthrobacter* and *Pseudomonas*, assuming a mode of application which would achieve substantially uniform contact of at least about 50% of the wheat head. If the antagonists are applied as a solid formulation, the rate of application should be controlled to result in a comparable number of viable cells per unit area of cereal head surface as obtained by the aforementioned rates of liquid treatment.

It is envisioned that the temperatures at which the antagonists are effective would range from about 5° C. to about 35° C. The preferred temperature range is 15-30° C., and the optimal range is considered to be 18-28° C.

The antagonists can theoretically be applied to the seed head at any time after the boot stage and before the hard dough stage of cereal development. The cereal head is only susceptible to infection by *F. graminearum* from the onset of flowering (anthesis) through the soft dough stage of kernel development. Thus, the best time to apply the biological control agents would be from the time immediately preceding flowering until as late as the soft dough stage of kernel development. Application of antagonists to heads before flowering would allow antagonists to have colonized wheat head parts prior to the wheat head becoming susceptible to infection. Additionally, antagonists would be well positioned to colonize and protect anthers as they emerge from florets. It is expected that the antagonists would still be effective if applied after flowering has begun, but before the hard dough stage of development. However, it is anticipated that long delays may decrease the effectiveness of the microbial treatment depending on methods of cell formulation and application.

The following examples are intended only to further illustrate the invention and are not intended to limit the scope of the invention which is defined by the claims.

EXAMPLE 1

Materials and Methods

Isolation of Wheat Anther Colonists

Procedures utilized to acquire a collection of microbial strains that were isolated from anthers are described elsewhere (Khan et al., 2001). Briefly, wheat anthers from across the states of Illinois and Ohio were collected using sterilized jeweler's forceps. Anthers were placed in vials containing 10% (v/v) glycerol at 5° C. immediately after collection and stored frozen at −80° C. until use. More than 400 anther collections were obtained. To isolate individual strains of microorganisms from anthers, vials were thawed until the glycerol suspension reached 4° C. Vials were then mixed using a vortex mixer for 30 sec to liberate microorganisms from anther surfaces. Suspensions containing microorganisms were then serially diluted using sterile, weak pH 7.2 phosphate buffer (0.004% w/v KH2PO4 buffer with 0.019% w/v MgCl2; Aid Pack, Gloucester, Mass.). Samples were plated onto a variety of solidified media (Khan et al., 2001). Single colonies of antagonists showing distinct growth morphology were streaked for purity on one-fifth strength Tryptic soy broth agar (TSBA/5, pH 6.8) (Difco Laboratories, Detroit, Mich.). Seven hundred thirty eight microbial isolates were purified and preserved in 10% w/v glycerol at −80° C. until needed.

Choline Utilization Test

Figure 2:
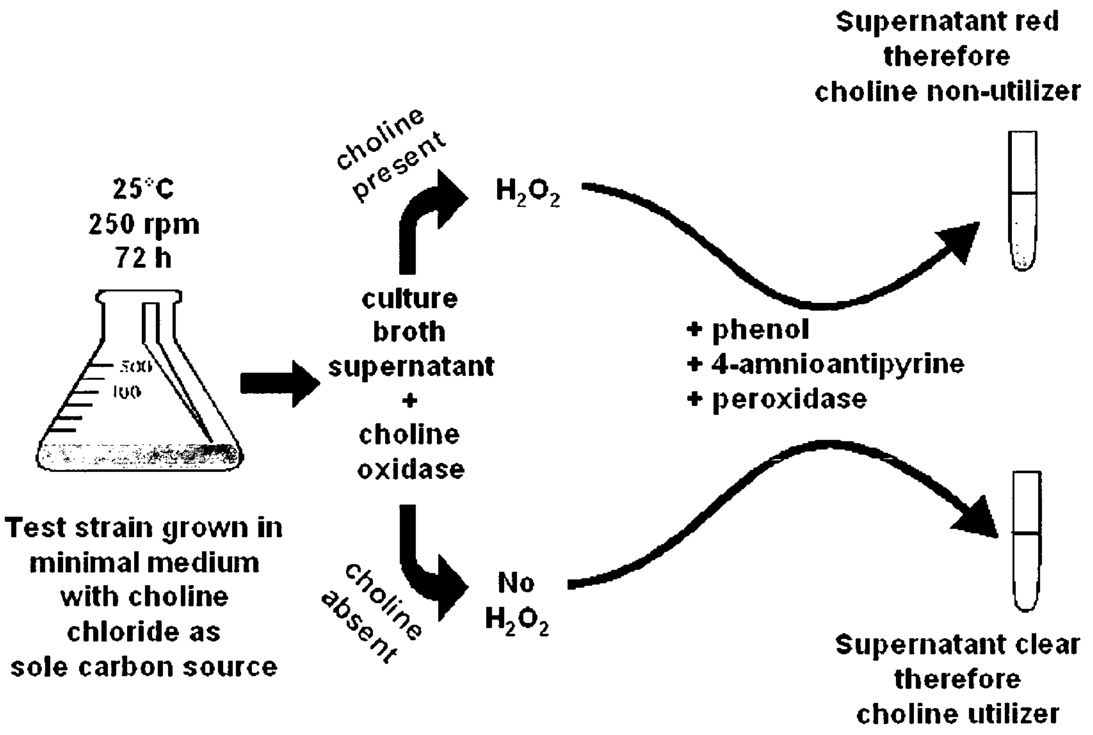
FIG. 2 shows a liquid culture assay for identifying microbial strains capable of utilizing choline as a sole carbon and nitrogen source.

Samples of cultures frozen at −80° C. in 10% glycerol were transferred to TSBA/5 and streaked for purity. Single colonies were then grown on TSBA/5 for 24 h at 28 C and used to heavily inoculate (optical density (OD) of approximately 0.5 at 620 nm wavelength light ($A_{620}$)) 10 ml of a minimal defined liquid medium (MDL, Slininger et al. 1994) in 50 ml Erlenmeyer flasks. Choline chloride (1 g/L) served as the sole carbon and nitrogen source in MDL. Cultures were incubated at 25° C. and 250 rpm for 72 h. Two milliliters of each culture broth were then centrifuged (5000 rpm or approximately 2000 RCF for 10 min at 4° C.) and the supernatants retained. Supernatants were analyzed for the presence of choline using a modification of a colorimetric procedure of Takayama et al. (1977) (FIGS. 1, 2). If choline is not fully metabolized by a microbial strain during growth, the addition of choline oxidase to spent broth produces hydrogen peroxide ($H_2O_2$) which, in the presence of phenol, 4-aminoantipyrine, and peroxidase produces 3H-Pyrazol-3-one, a dye which colors the reaction fluid red (FIGS. 1,2). Conversely, for a strain which utilized all available choline during the 72 h growth period, $H_2O_2$ would not be produced in the presence of choline oxidase and a choline-utilizing strain (CUS) could then be identified by the lack of formation of a red color when spent broth and the "colorizing reagents" (CR) were combined. One liter of CR is composed of 1000 units choline oxidase (from *Alcaligenes* species, Sigma-Aldrich, St. Louis), 2200 units of peroxidase (Type XII from horseradish, Sigma-Aldrich, St. Louis), 0.12 g 4-aminoantipyrine, 0.20 g phenol, 0.08 g calcium chloride dihydride, 6.99 g Tris HCl, and 2 ml Triton X-100 wetting agent. Individual tests of spent culture broths were conducted by combining 6.7 uL of spent broth with 1 ml CR, incubating for 15 minutes at 37° C. and assessing the presence or absence of color development. Uninoculated broth served as a control to ascertain the maximum color intensity that would be obtained when a test strain utilized none of the 1 g/L choline chloride present in the growth medium.

Greenhouse Testing of Choline-Utilizing Strains (CUS)

Two seedlings of hard red spring wheat (cultivar Norm) per 19-cm diameter pot were grown in an air-steam pasteurized (60° C. for 30 min) potting mix (Terra-lite Redearth mix, W. R. Grace, Cambridge, Mass.) in a growth chamber (25° C., 14 h light/day, 600 mol/($m^2$/sec)) for approximately 8 weeks prior to transfer to greenhouse benches for use in biocontrol bioassays. Conidial inoculum of *G. zeae* isolate Z-3639 was produced on clarified V8 juice agar (CV8 agar) under 12 h/day fluorescent light for 7 days at 24° C. (Schisler & Slininger, 1994). Suspensions of macroconidia were obtained by flooding the surface of colonized CV8 agar with $PO_4$ buffer, dislodging conidia using a sterile inoculating loop and adjusting the concentration of conidia to $5\times10^5$ conidia/ml. To produce CUS biomass, cells were grown on TSBA/5 for 24 h as described above. These cells were then used to inoculate (optical density (OD) of approximately 0.2 at 620 nm wavelength light ($A_{620}$)) 10 ml of a semidefined liquid medium (SDCL, Slininger et al. 1994) in 50 ml Erlenmeyer flasks. Flasks were incubated at 25° C. and shaken at 250 rpm for 48 h. At wheat anthesis, colonized broth of a CUS was diluted 1:3 (v/v) with an aqueous solution of 0.04% Tween 80 in weak phosphate buffer (approximately $2\times10^9$ CFU/ml and $5\times10^8$ CFU/ml for bacteria and yeast strains, respectively). Cell suspensions were then misted until run-off onto 12 wheat heads, or four plants, followed immediately by a mist application of a suspension of conidia of *G. zeae* Z-3639 ($5\times10^5$ conidia/ml). Heads treated with the buffer/TWEEN solution followed by the conidial suspension served as "pathogen only" controls. Plants were placed in plastic humidity chambers (22-26° C.) consisting of a PVC pipe frame covered with clear plastic, removed after 3 days, and scored for disease severity after 16 days using a 0-100% scale (Stack & McMullen, 1995). Due to experimental size constraints, multiple experiments were conducted in order to test 116 full, 7 partial CUS. More than 30 greenhouse experiments were conducted in the screening of CUS. In cases where strains were tested more than once due to excessive disease development in the assay, results are presented from an experimental repeat where more moderate disease pressure was obtained. In order to compare the influence of CUS from different experiments using a normalized scale, disease severity values for heads treated with a specific CUS were expressed as a percentage increase or decrease in severity compared to the disease severity of the control for the same experiment.

Field Testing of CUS

CUS that were superior in reducing FHB disease severity compared to controls in the greenhouse bioassay were selected for field trials. An isolate of an *Arthrobacter* sp. was also selected for field testing due to strains in the genus characteristically possessing desiccation tolerance and competitiveness due to breadth of carbon source utilization. Field trials using 6 CUS were first conducted at Peoria, Ill. and Wooster, Ohio (data not shown), and then using 1 of these 6 CUS strains and 4 additional CUS strains (Table 1). Soft red winter wheat cultivars Freedom (moderately FHB resistant) and Pioneer Brand 2545 (FHB susceptible) were utilized at both experimental locations. Recently, the fungicide Folicur 3.6F (38.7% tebuconazole, Bayer Crop Science, Kansas City, Mo.) has received yearly emergency exemption for the management of FHB in several States in the United States and was therefore included in the field trials as the only available fungicide for field application during wheat flowering.

Antagonist and Pathogen Inoculum Production

Cells of antagonists were taken from −80° C. cold storage and grown on TSBA/5 for 24 h as described above. Cells of individual strains then were harvested and used to seed pre-cultures consisting of 100 ml of SDCL in 500 ml flasks (OD of 0.10 at $A_{620}$). Flasks were incubated at 25° C. at 250 rpm (2.5 cm eccentricity) for 24 h. Pre-cultures then were used to seed 3 L Fernbach flasks containing 1.5 liters of SDCL to an OD of 0.10. Cultures were incubated for 48 h at 25° C. and 250 rpm. Colonized broth then was transferred to sterile containers, transported to the field on ice and used within 24 h. Inoculum of *G. zeae* was prepared on sterile, yellow dent corn as described by Khan et al. (2004). Briefly, yellow-dent corn kernels were soaked in water for 24 h, drained, placed in an autoclavable vessel, and autoclaved for 1 h on two consecutive days. Kernels were then inoculated with *G. zeae* strain Fg 111-B for the Peoria, Ill. field trial and *G. zeae* Fg 3-93 or Fg 6-93 for the Wooster, Ohio field trial. Pathogen strains were isolated from diseased wheat grown in the local area in previous years. Vessels were shaken periodically during 2 weeks' incubation at 25° C. Infested corn kernels were then removed from vessels, individual kernels separated, and used immediately to inoculate field plots.

Field Test in Peoria, Ill.

In Peoria, Ill., an Orthents complex, with a silty loam surface layer of approximately 25 cm and underlying silty clay loam was conventionally cultivated in the fall after application of 1120 kg/ha of Parker's Super Soilife 10-10-10 (Pursell Industries, Inc., Sylacauga, Ala.) (3.92% ammonium nitrate, 6.68% urea nitrogen (1.7% slow release)). Rows of Pioneer 2545 (2.1 m long) were planted by hand with 0.3 m between rows. Rows of a cultivar planting were separated from rows of the other cultivar by 0.3 m walkways. A border row of Pioneer Brand 2545 surrounded the experiment site and was not treated. The following spring, two to three weeks before the anticipated date of wheat flowering, 20 kernels/$m^2$ of yellow dent corn colonized by *G. zeae* were applied uniformly by hand to the site. Perithecia appeared on the kernels after about 10 days and were releasing ascospores at the time of wheat anthesis. Prior to application to flowering wheat heads, colonized culture broths were diluted to 50% of full strength using weak phosphate buffer. TWEEN-80 was added to microbial suspensions to a final concentration of 0.036% (v/v). Final CFU/ml counts for antagonist treatments were approximately $1\times10^9$ CFU/ml and $6\times10^7$ CFU/ml for bacteria and yeast strains, respectively. Treatment suspensions were applied using a $CO_2$ backpack sprayer charged at 2.8 kg/$cm^2$ and attached to a boom equipped with two, #6 Cone-jet® nozzles (R&D Sprayers, Opelousas, La.) spaced 30 cm apart and mounted pointing inward at 45 degrees. Treatment suspensions were charged with $CO_2$ just prior to application. Treatments were applied at 750 l/ha just prior to and continuing after sunset to minimize potential UV degradation of antagonist cells. There were 5 replicates per treatment which were arranged in a randomized block design. The primary control treatment consisted of plants treated with a solution of buffer/TWEEN. A second control consisted of untreated plants. Treatment applications were contained to individual rows using two PVC pipe frames covered by plastic that were placed on either side of a row to be treated. The PVC pipe frames were thoroughly rinsed after each treatment application. From the morning after treatment application until mid-milk kernel development (Feekes growth stage 11.1, (Large, 1954)), wheat heads were misted with city water for 10 min/h from 5:00 PM until 12:00 AM and 2 min/h from 12:00 AM until 7:00 AM (approximately 2 cm water/day). Rainbird nozzles (15H, 15' 180 degree and 15Q, 15; 90 degree nozzles and PA-8S plastic shrub adapters) (Azusa, Calif.) mounted on 1.2 m risers were spaced to provide equivalent water coverage across the entire plot.

Field assessments of FHB severity and incidence were made by evaluating 60 heads per replicate (300 heads/treatment) when plants were between mid-milk and soft dough development (Feekes 11.1-11.2). Wheat heads were harvested by hand and threshed using an Almaco thresher when grain reached full maturity. Grain samples obtained from each replicate row were evaluated for 100-kernel weight. Disease severity, incidence, and 100 kernel weight data were analyzed using one-way analysis of variance (ANOVA) after preliminary analysis revealed significant block by treatment interactions for the majority of disease parameters. Means were separated from the untreated and the buffer/TWEEN controls at P=0.05 using Fisher's protected LSD test (Statistix 7.0, Tallahassee Fla.).

Field Test in Wooster, Ohio

In the fall, seeds of Pioneer Brand 2545 and Freedom wheat were planted at a rate of approximately 24 seeds/ft of row in Ravenna silt loam using a Hege 1000 Series plot planter at the Ohio Agricultural Research and Development Center near Wooster, Ohio. Prior to planting, the field was mold-board plowed and 84.2 Kg/ha of ammonium nitrate was broadcast over the field and incorporated with a disc. The experimental treatments were arranged in a randomized block design with 4 and 5 replicate plots for Freedom and Pioneer Brand 2545, respectively. Each experimental unit consisted of a 7-row plot that was 1 m×1 m. Additional nitrogen was applied the following spring as 109 kg of ammonium nitrate. Plots were inoculated by broadcasting corn kernels infested with *G. zeae* over the plot surface approximately 3 weeks prior to wheat flowering. The plot was mist irrigated using NAAN 7110 series bridge with mist sprayer head 327122 fitted with nozzles having 0.35 in. openings that provided 10.2 GPH. Plots were mist irrigated each day from 1 wk prior to flowering to 2 wk after flowering. The mist irrigation operated for 2.5 min out of each 10 min from 6:00 to 10:00 AM and from 8:00 to 10:00 PM each day. The mist irrigation system consisted of 0.9 m tall risers with two mist nozzles at the end of 1.54 m wide arms. Risers were spaced every 2.4 m. Nozzles were NAAN 7110 Series Bridge with a mist sprayer head (no. 327122) and a nozzle (no. 5920910) with a 0.89 mm opening (Waldo and Associates, Inc. Perrysburg, Ohio). The nozzle output was 38.6 liters/h at 2.8 kg/$cm^2$ covering a 2 m diameter area. Triademafon (140 g a.i. in 337 liters/ha) was applied as a foliar spray at early boot growth stage to control powdery mildew (*Blumeria graminis* f. sp. *tritici* (DC. Em. Marchal)) and *Stagonospora glume* blotch (*Stagonospora nodorum* (Berk.) E. Castell. & Germano). Treatments were as described for the Peoria, Ill. trial and were applied at 750 l/ha with a $CO^2$-pressurized back pack sprayer as described above except that 2 twinjet XR8001VS nozzles were mounted 38 cm apart and at 60 degrees inwards.

Field assessments of FHB severity and incidence were made by evaluating 45 heads per replicate (180 and 225 heads/treatment for cultivars Freedom and Pioneer Brand 2545, respectively) when plants were between mid-milk and soft dough development (Feekes 11.1-11.2). Wheat heads were harvested by hand and threshed using an Almaco thresher when grain reached full maturity. Two grain samples obtained from each replicate plot were evaluated for 100-kernel weight. Disease severity, incidence, and 100 kernel weight data were analyzed using one-way ANOVA analysis of variance after preliminary analysis revealed significant block by treatment interactions for the majority of disease parameters. Means were separated from the untreated and the buffer/TWEEN controls at P=0.05 using Fisher's protected LSD test (Statistix 7.0, Tallahassee Fla.).

Results

Choline Utilization Test

A total of 738 microbial strains were recovered from wheat anthers collected across the states of Illinois and Ohio. Of this total, 122 choline utilizing strains (CUS) were identified (16.5%) when choline chloride was supplied as a sole carbon and nitrogen source in liquid culture and culture filtrates were analyzed for choline using a calorimetric, choline oxidase-based bioassay. Of the strains isolated from wheat anthers collected in Illinois, 94 of 514 fully utilized choline while 23 of 237 strains obtained from anthers collected in Ohio fully utilized choline. Eleven additional strains partially utilized choline during 72 h growth (Table 1) as determined by the production, in test supernatants, of measurable color of less intensity than produced when testing uninoculated control broths.

Greenhouse Testing of Choline-Utilizing Strains (CUS)

Thirty-one out of 123 CUS (116 full, 7 partial) (25% of all strains tested) reduced FHB disease severity by at least 25% compared to "disease only" controls in greenhouse tests (Table 1) and 17 (14% of all strains tested) reduced FHB severity by at least 50%. Several strains which substantially reduced FHB severity compared to the control were not selected for field testing due to the strain possessing similar colony morphology to other strains from the same anther sample or a presumptive identification placing the strain in a genus that would be of questionable utility for commercial development. Ten CUS with FHB biocontrol activity in greenhouse assays were selected for field testing (Table 1). One strain that reduced FHB symptoms in first field tests (AS 64.4) and 4 strains not previously field tested were selected for replicate subsequent field trials in Peoria, Ill. and Wooster, Ohio. These CUS were identified as members of the genera *Erwinia, Pantoea, Aureobasidium, Pseudomonas* and *Arthrobacter* (Table 2) by MIDI Labs (Newark, Del.) using 16S or large subunit rDNA gene sequence homologies with known strains as determined by Applied Biosystems MicroSeq™ microbial analysis software and database (Foster City, Calif.).

Field Testing of CUS

Field Test in Peoria, Ill.

In plots of cultivar Freedom, FHB severity was low (less than 2% in all experimental plots). Wheat treated with any of the five CUS had lower FHB severity and incidence compared to the "untreated" control (P=0.05) with AS 64.4 and AS 35.5 treated wheat at 63% and 58% of the severity level of the control, respectively (Table 3). The "buffer/TWEEN" control and wheat treated with the fungicide Folicur 3.6F also had less severity and incidence than the untreated control (Table 3). The 100 kernel weights of wheat harvested from treated plots did not different significantly.

In Peoria plots of cultivar Pioneer 2545, Folicur 3.6F treated wheat had lower disease severity than in either control plot while wheat treated with 3 of the 5 CUS had reduced disease severity compared to the "untreated" control. Wheat treated with the same 3 CUS had less FHB incidence than the untreated control as did wheat treated with Folicur 3.6F. Strain AS 64.4 and Folicur 3.6F treated wheat had 41% and 38% of the incidence level of the control (Table 3). Wheat treated with CUS or fungicide did not differ in 100 kernel weight compared to the untreated control though all treated wheat had lower 100 kernel weights than that of the "buffer/TWEEN" control.

Field Test in Wooster, Ohio

Disease pressure was high in Wooster, Ohio, on both cultivars Freedom and Pioneer 2545. In Freedom wheat, FHB severity was less in plots treated with all CUS and Folicur 3.6F than in the untreated check and wheat treated with 3 of the 5 CUS and Folicur 3.6F had less FHB severity than the "buffer/TWEEN" control wheat (P=0.05). Reductions in severity for wheat treated with AS 64.45 and Folicur 3.6F were 46% and 54% compared to untreated wheat. The incidence of FHB was also less in plots treated with CUS AS 64.4 and Folicur 3.6F compared to either control. Regardless of the treatment used, 100 kernel weights in treated plots did not differ from the control plots.

In Wooster plots of cultivar Pioneer 2545, wheat treated with any of the five CUS or Folicur 3.6F had lower FHB severity than at least one of the controls (P=0.05). Wheat treated with AS 55.2 had the lowest disease severity of any of the wheat treatments though damage was still severe on treated plots. All treated wheat had near 100% incidence and the 100 kernel weights of wheat from treated plots did not differ significantly.

REFERENCES

AOKI, T., & O'DONNELL, K. (1999) Morphological and molecular characterization of *Fusarium pseudograminearum* sp. nov., formerly recognized as the Group 1 population of *F. graminearum*. Mycologia 91, 597-609.

BAI, G.-H., SHANER, G., & OHM, H. (2000) Inheritance of resistance to *Fusarium graminearum* in wheat. Theoretical and Applied Genetics. 100, 1-8. SUBSTITUTE BAI/SHANER 2004 ANNUAL REVIEW PHYTOPATH ARTICLE (COPY OF IT IN MY LIT)

BEARDALL, J. M. & MILLER, J. D. (1994) Diseases in humans with mycotoxins as possible causes, in Mycotoxins in Grain: Compounds Other than Aflatoxin (MILLER, J. D. & TRENHOLM, H. L., Eds.). Eagan Press, St. Paul, Minn., pp. 387-539.

BUJOLD, I., PAULITZ, T. C., & CARISSE, O. (2001) Effect of *Microsphaeropsis* sp. on the production of perithecia and ascospores of *Gibberella zeae*. Plant Disease 85, 977-984.

BUSHNELL, W. R., SOMERS, D. A., GIROUX, R. W., SZABO, L. J. & ZEYEN, R. J. (1998) Genetic engineering of disease resistance in cereals. Canadian Journal of Plant Pathology 20, 137-149.

CARDWELL, K. F., DESJARDINS, A., HENRY, S. H., MUNKVOLD, G., & ROBENS, J. (2001) Mycotoxins: the cost of achieving food security and food quality. APS Net (www.apsnet.org): Feature story August, 2001.

CHEN, L. F., BAI, G. H., & DESJARDINS, A. E. (2000) Recent advances in wheat head scab research in China, in Proc. Int. Symp. Wheat Improvement for Scab Resistance (RAUPP, W. J., MA, Z., CHEN, P. & LIU, D., Eds.). Nanjing Agricultural University, Jiangsu, China, pp. 258-273.

CHONGO, G., GOSSEN, B. D., KUTCHER, H. R., GILBERT, J., TURKINGTON, T. K., FERNANDEZ, M. R., and McLAREN, D. (2001) Reaction of seedling roots of 14 crop species to *Fusarium graminearum* from wheat head. Canadian Journal of Plant Pathology 23, 132-137.

CUMAGUN, C. J. R., BOWDEN, R. L., JURGENSON, J. E., LESLIE, J. F., & MIEDANER, T. (2004) Genetic mapping of pathogenicity and aggressiveness of *Gibberella zeae* (*Fusarium graminearum*) toward wheat. Phytopathology 94, 520-526.

DILL-MACKY, R. & JONES, R. K. (2000) The effect of previous crop residues and tillage on *Fusarium* head blight of wheat. Plant Disease 84, 71-76.

DUFFY, B. K., SIMON, A., & WELLER, D. M. (1996) Combinations of *Trichoderma knoingii* with fluorescent pseudomonads for control of take-all on wheat. Phytopathology 86, 188-194.

DUFFY, B., KEEL, C. & DEFAGO, G. (2004) Potential role of pathogen signaling in multitrophic plant-microbe interactions involved in disease protection. Applied and Environmental Microbiology 70, 1836-1842.

ELMER, W. H. & MCGOVERN, R. J. (2004) Efficacy of integrating biologicals with fungicides for the suppression of *Fusarium* wilt of cyclamen. Crop Protection 23, 909-914.

ENGLE, J. S., LIPPS, P. E., GRAHAM, T. L. & BOEHM, M. J. (2004) Effects of choline, betaine, and wheat floral extracts on growth of *Fusarium graminearum*. Plant Disease 88, 175-180.

GALE, L. R., CHEN, L. F., HERNICK, C. A., TAKAMURA, K. & KISTLER, H. C. (2002) Population analysis of *Fusarium graminearum* from wheat fields in eastern China. Phytopathology 92, 1315-1322.

GILBERT, J. & FERNANDO, W. G. D. (2004) Epidemiology and biological control of *Gibberella zeae* (anamorph *Fusarium graminearum*). Canadian Journal of Plant Pathology 26, 1-9.

HESSELTINE, C. W., ROGERS, R. F. & SHOTWELL, O. (1978) Fungi, especially *Gibberella zeae*, and zearalenone occurrence in wheat. Mycologia 70, 14-18.

JACKSON, M. A., CLIQUET, S., & ITEN, L. B. (2003) Media and fermentation processes for the rapid production of high concentrations of stable blastospores of the bioinsecticidal fungus *Paecilomyces fumosoroseus*. Biocontrol Science and Technology 13, 23-33.

JOHNSTON, H. W. (1994) Resistance in advanced winter wheat breeding lines to scab, 1993. Biological and Cultural Tests 9, 119.

JONES, R. K. (1999) Seedling blight development and control in spring wheat damaged by *Fusarium graminearum* Group 2. Plant Disease 83, 1013-1018.

KHAN, N. I., SCHISLER, D. A., BOEHM, M. J., LIPPS, P. E., & SLININGER, P. J. (2004) Field testing of antagonists of *Fusarium* head blight incited by *Gibberella zeae*. Biological Control 29, 245-255.

KHAN, N. I., SCHISLER, D. A., BOEHM, M. J., SLININGER, P. J. & BOTHAST, R. J. (2001) Selection and evaluation of microorganisms for biocontrol of *Fusarium* head blight of wheat incited by *Gibberella zeae*. Plant Disease 85, 1253-1258.

KIEFT, T. L, RINGELBERG, D. B. & WHITE, D. C. (1994) Changes in ester-linked phospholipids fatty acid profiles of subsurface bacteria during starvation and desiccation in a porous medium. Applied and Environmental Microbiology 60, 3292-3299.

LARGE, E. C. (1954) Growth stages in cereals. Illustrations of the Feekes scale. Plant Pathology 3, 128 129.

LEGZDINA, L. & BUERSTMAYR, H. (2004) Comparison of infection with *Fusarium* head blight and accumulation of mycotoxins in grain of hulless and covered barley. Journal of Cereal Science 40, 61-67.

LUTZ, M. P., WENGER, S., MAURHOFER, M., DEFAGO, G. & DUFFY, B. (2004) Signaling between bacterial and fungal biocontrol agents in a strain mixture. FEMS Microbiology Ecology 48, 447-455.

LUZ, W. C. da, STOCKWELL, C. A. & BERGSTROM, G. (2003) Biological control of *Fusarium graminearum*, in *Fusarium* head blight of wheat and barley (LEONARD, K. J. & BUSHNELL, W. R., Eds.) APS Press, St. Paul, Minn., 381-394.

MARASAS, W. F. O. (1991) Toxigenic Fusaria, in: Mycotoxins and Animal Foods, J. E. Smith and R. S. Henderson, eds., CRC Press, Inc., Boca Raton, Fla.

MAULER-MACHNIK, A. & ZAHN, K. (1994) Ear fusarioses in wheat-new findings on their epidemiology and control with Folicur (tebuconazole). Pflanzenschutz-Nachrichten Bayer 47, 129-155.

McCALLUM, B. D., TEKAUZ, A. & GILBERT, J. (2004) Barrage zone formation between vegetatively incompatible *Fusarium graminearum* (*Gibberella zeae*) isolates. Phytopathology 94, 432-437.

McMULLEN, M., JONES, R. & GALLENBERG, D. (1997) Scab of wheat and barley: are emerging disease of devastating impact. Plant Disease 81, 1340-1348.

MILLER, J. D., CULLEY, J., FRASER, K., HUBBARD, S., MELOCHE, F., OUELLET, T., SEAMAN, W. L., SEIFERT, K. A., TURKINGTON, K. & VOLDENG, H. (1998) Effect of tillage practice on *Fusarium* head blight of wheat. Canadian Journal of Plant Pathology 20, 95-103.

MILUS, E. A., HERSHMAN, D. & McMULLEN, M. (2001) Analysis of the 2001 uniform wheat fungicide and biocontrol trials across locations, in Proceedings of the 2001 National *Fusarium* Head Blight Forum, Kinko's, Okemos, Mich., pp. 75-79.

MONTAZERI, M. & GREAVES, M. P. (2002) Effects of nutrition on desiccation tolerance and virulence of *Colletotrichum truncatum* and *Alternaria alternata* conidia. Biocontrol Science and Technology 12, 173-181.

MUTHOMI, J. W., OERKE, E. C., DEHNE, H. W. & MUTITU, E. W. (2002) Susceptibility of Kenyan wheat varieties to head blight, fungal invasion and deoxynivalenol accumulation inoculated with *Fusarium graminearum*. Journal of Phytopathology 150, 30-36.

NKONGOLO, K. K., DOSTALER, D., & COUTURE, L. (1993) Effet de la betaine, de la choline et d'extraits d'antheres du blé sur la croissance du *Fusarium graminearum*. Canadian Journal of Plant Pathology 15, 81-84.

O'DONNELL, K., WARD, T. J., GEISER, D. M., KISTLER, H. C. & AOKI, T. (2004) Genealogical concordance between the mating type locus and seven other nuclear genes supports formal recognition of nine phylogenetically distinct species within the *Fusarium graminearium* clade. Fungal Genetics and Biology 41, 600-623.

OLIVAIN, C., ALABOUVETTE, C. & STEINBERG, C. (2004) Production of a mixed inoculum of *Fusarium oxysporum* Fo47 and *Pseudomonas fluorescens* C7 to control *Fusarium* diseases. Biocontrol Science and Technology 14, 227-238.

PAULITZ, T. C. (1999) *Fusarium* head blight: a re-emerging disease. Phytoprotection 80, 127-133.

PEREYRA, S. A., DILL-MACKY, R. & SIMS, A. L. (2004) Survival and inoculum production of *Gibberella zeae* in wheat residue. Plant Disease 88, 724-730.

PERONDI, N. L., LUZ, W. C. da & THOMAS, R. (1996) Controle microbiológico da giberela do trigo. Fitopatologia Brasiliera 21, 243-249.

PESTKA, J. J. & BONDY, G. S. (1994) Immunotoxic effects of mycotoxins, in Mycotoxins in Grain: Compounds Other than Aflatoxin (MILLER, J. D. & TRENHOLM, H. L., Eds.) Eagan Press, St. Paul, Minn., pp. 339-358.

PRITSCH, C., VANCE, C. P., BUSHNELL, W. R., SOMERS, D. A., HOHN, T. M.& MUEHLBAUER, G. J. (2001) Systemic expression of defense response genes in wheat spikes as a response to *Fusarium graminearum* infection. Physiological and Molecular Plant Pathology 58, 1-12.

RAMIREZ, M. L., CHULZE, S. & MAGAN, N. (2004) Impact of environmental factors and fungicides on growth and deoxynivalenol production by *Fusarium graminearum* isolates from Argentinian wheat. Crop Protection 23, 117-125.

SCHISLER, D. A. & SLININGER, P. J. (1994) Selection and performance of bacterial strains for biologically controlling *Fusarium* dry rot of potatoes incited by *Gibberella pulicaris*. Plant Disease 78, 251-255.

SCHISLER, D. A., JACKSON, M. A. & BOTHAST, R. J. (1991) Influence of nutrition during conidiation of *Colletotrichum truncatum* on conidial germination and efficacy in inciting disease on Sesbania exaltata. Phytopathology 81, 587 590.

SCHISLER, D. A., SLININGER, P. J. & BOTHAST, R. J. (1997) Effects of antagonist cell concentration and two-strain mixtures of biological control of *Fusarium* dry rot of potatoes. Phytopathology 87, 177-183.

SCHISLER, D. A., BOEHM, J. J., HICKS, T. E. & LIPPS, P. E. (2002a) USDA-ARS, Ohio State University cooperative research on biologically controlling *Fusarium* head blight 2:2002 field tests of antagonist and antagonist/fungicide mixtures, in Proceedings of the 2002 National *Fusarium* Head Blight Forum, Kinko's, Okemos, Mich., pp. 119-122.

SCHISLER, D. A., KHAN, N. I, & BOEHM, M. J. (2002b) Biological control of *Fusarium* head blight of wheat and deoxynivalenol levels in grain via use of microbial antagonists, in Mycotoxins and Food Safety (DeVRIES, J. W., TRUCKSESS, M. W. & JACKSON, L. S., Eds.). Kluwer Academic/Plenum Publishers, New York, pp. 53-69.

SCHISLER, D. A., KHAN, N. I., BOEHM, M. J., & SLININGER, P. J. (2002c) Greenhouse and field evaluation of biological control of *Fusarium* head blight on durum wheat. Plant Disease 86, 1350-13.56.

SCHISLER, D. A., KHAN, N. I, BOEHM, M. J., ZHANG, S. & SLININGER, P. J. (2004) Selection and field evaluation of choline-utilizing microbial strains as potential biocontrol agents of *Fusarium* head blight. Phytopathology 94, S93.

SLININGER, P. J., SCHISLER, D. A. & BOTHAST, R. J. (1994) Two-dimensional liquid culture focusing: a method of selecting commercially promising microbial isolates with demonstrated biological control capability. Improving Plant Productivity with Rhizosphere Bacteria, 3rd International Workshop on Plant Growth-Promoting Rhizobacteria, Adelaide, S. Australia. (RYDER, M. H. et al., Eds) Graphic Services, Adelaide, Australia. CSIRO Division of Soils: Glen Osmond. pp. 29-32.

SLININGER, P. J., VANCAUWENBERGE, J. E., BOTHAST, R. J., WELLER, D. M., THOMASHOW; L. S., & COOK, R. J. (1996) Effect of growth culture physiological state, metabolites, and formulation on the viability, phytotoxicity, and efficacy of the take-all biocontrol agent *Pseudomonas fluorescens* 2-79 stored encapsulated on wheat seeds. Applied Microbiology and Biotechnology 45, 391-398.

SNIJDERS, C. H. A. (1990) *Fusarium* head blight and mycotoxin contamination of wheat, a review. Netherlands Journal of Plant Pathology 96, 187-198.

STACK, R. W. & McMULLEN, M. P. (1995) A visual scale to estimate severity of *Fusarium* head blight in wheat. North Dakota State University Extension Service Bulletin PP-1095.

STRANGE, R. N. & SMITH, H. (1971) A fungal growth stimulant in anthers which predisposes wheat to attack by *Fusarium graminearum*. Physiological Plant Pathology 1, 141-150.

STRANGE, R. N. & SMITH, H. (1978) Specificity of choline and betaine as stimulants of *Fusarium graminearum*. Transactions of the British Mycological Society 70, 187-192.

SUTY, A. & MAULER-MACHNIK, A. (1997) *Fusarium* ear blight on wheat-epidemiology and control of *Gibberella zeae*, the teleomorph of *Fusarium graminearum* with Folicur, in Diagnosis and Identification of Plant Pathogens, Proceedings of the 4th International Symposium of the European Foundation for Plant Pathology (DEHNE, H.-W., ADAM, G., DIEKMANN, M., FRAHM, J., MAULER-MACHNIK & VAN HALTEREN, P., Eds). Kluwer Academic Publishers, Dordrecht., pp. 243-246.

TAKAYAMA, M., ITOH, S., NAGASAKI, T., & TANIMIZU, I. (1977) A new enzymatic method for determination of serum choline-containing phospholipids. Clinica chimica acta 79, 93-98.

WALKER, S. L., LEATH, S., HAGLER, W. M., Jr. & MURPHY, J. P. (2001) Variation among isolates of *Fusarium graminearum* associated with *Fusarium* head blight in North Carolina. Plant Disease 85, 404-410.

WILCOXSON, R. D. (1996) Fungicides for control of *Fusarium* head blight. Int. J. Tropical Plant Disease 14, 27-50.

YU GAGKAEVA, T. & YLI-MATTILA, T. (2004) Genetic diversity of *Fusarium graminearum* in Europe and Asia. European Journal of Plant Pathology 110, 551-562.

ZHANG, S., SCHISLER, D. A., BOEHM, J. J., & SLININGER, P. J. (2003) USDA-ARS, Ohio State University cooperative research on biologically controlling *Fusarium* head blight 2: effect of carbon-to-nitrogen ratio of production media on the biocontrol efficacy and the survival of *Cryptococcus* nodaensis OH 182.9 after freeze-drying, in Proceedings of the 2003 National *Fusarium* Head Blight Forum, Kinko's, Okemos, Mich., pp. 116-117.

It is understood that the foregoing detailed description is given merely by way of illustration and that modifications and variations may be made therein without departing from the spirit and scope of the invention.

TABLE 1

Efficacy of selected choline-utilizing strains (CUS) in reducing FHB severity in greenhouse bioassays[ab]

| CUS Strain | Strain Notes | Greenhouse Experiment Number | % Change in FHB Severity vs pathogen control[c] |
|---|---|---|---|
| AS 11.1 | | 1 | −3 |
| AS 11.2 | | 1 | −3 |
| AS 11.4 | | 1 | −3 |
| AS 12.3 | | 1 | −4 |
| AS 13.5 | | 1 | −9 |
| AS 13.7 | | 1 | −10 |
| **AS 35.5** | **f** | **2** | **−69** |
| AS 36.1 | | 2 | −57 |
| AS 36.2 | | 3 | −46 |
| AS 36.3 | | 2 | −4 |
| AS 36.4 | | 2 | −6 |
| AS 36.5 | | 2 | −23 |
| AS 36.6 | | 2 | −4 |
| AS 36.7 | | 4 | −25 |
| AS 36.8 | | 4 | −19 |
| AS 38.1 | | 4 | −37 |
| AS 38.3 | | 4 | −42 |
| AS 49.1 | | 4 | −55 |
| AS 49.2 | | 4 | −38 |
| AS 49.3 | | 5 | 0 |
| AS 49.4 | | 5 | −5 |
| AS 49.5 | | 5 | 0 |
| AS 49.6 | | 5 | −5 |
| AS 49.7 | | 5 | −2 |
| AS 49.8 | | 5 | −4 |
| AS 49.9 | | 5 | 0 |
| AS 49.10 | | 6 | −30 |
| AS 51.3 | | 7 | 0 |
| AS 51.4 | | 7 | −6 |
| AS 51.5 | | 6 | 26 |
| AS 52.1 | | 7 | −17 |
| **AS 52.2** | **f** | **7** | **−57** |
| AS 52.3 | | 8 | −13 |
| AS 52.4 | | 6 | −16 |
| AS 52.5 | e | 9 | −81 |
| AS 52.6 | | 9 | −70 |
| AS 52.7 | | 9 | −69 |
| AS 52.8 | e | 3 | −48 |
| AS 54.3 | | 7 | −14 |
| AS 54.4 | e | 9 | −91 |
| AS 54.5 | | 9 | −74 |
| AS 54.7 | d | 10 | −2 |
| AS 54.8 | | 11 | −28 |
| AS 54.9 | | 11 | −35 |
| AS 55.1 | | 7 | −11 |
| **AS 55.2** | **f** | **11** | **−84** |
| AS 55.3 | d | 10 | −8 |
| AS 55.4 | d | 10 | 2 |
| AS 57.1 | e | 3 | −91 |
| AS 57.2 | | 11 | −81 |
| AS 57.3 | | 11 | −31 |
| AS 57.4 | | 12 | −56 |
| AS 57.5 | | 13 | 0 |
| AS 57.6 | | 13 | −14 |
| AS 58.2 | d, e | 3 | −89 |
| AS 59.1 | | 13 | 0 |
| AS 59.2 | | 13 | 0 |
| AS 59.3 | | 13 | −17 |
| AS 59.4 | | 14 | −26 |
| AS 59.5 | | 14 | 3 |
| AS 60.1 | | 15 | 6 |
| AS 60.2 | | 15 | −16 |
| AS 60.3 | | 16 | −8 |
| AS 60.4 | | 15 | 4 |
| AS 61.1 | | 15 | 8 |
| AS 61.2 | | 15 | 8 |
| AS 61.3 | | 17 | −3 |
| AS 61.4 | | 17 | 0 |
| AS 64.2 | | 18 | −54 |
| **AS 64.4** | **e, f** | **3** | **−83** |
| AS 64.5 | | 18 | −10 |
| AS 67.1 | | 18 | −24 |

TABLE 1-continued

Efficacy of selected choline-utilizing strains (CUS) in reducing FHB severity in greenhouse bioassays[ab]

| CUS Strain | Strain Notes | Greenhouse Experiment Number | % Change in FHB Severity vs pathogen control[c] |
|---|---|---|---|
| AS 67.2 | | 3 | −31 |
| AS 67.4 | | 17 | 0 |
| AS 68.1 | | 17 | 0 |
| AS 68.5 | | 17 | 0 |
| AS 70.1 | | 18 | 0 |
| AS 71.1 | | 3 | −53 |
| AS 71.3 | | 19 | −10 |
| AS 71.4 | | 19 | −8 |
| AS 71.5 | | 19 | 0 |
| AS 72.1 | | 19 | −2 |
| AS 72.2 | | 19 | 0 |
| AS 72.3 | | 20 | 7 |
| AS 72.4 | | 20 | 7 |
| AS 72.5 | | 20 | 3 |
| AS 73.2 | d | 20 | 7 |
| AS 75.3 | | 21 | 0 |
| AS 77.1 | d | 20 | 7 |
| AS 84.2 | | 22 | −6 |
| AS 84.4 | | 20 | 7 |
| AS 84.5 | | 22 | −6 |
| AS 86.5 | | 22 | 0 |
| AS 87.1 | | 22 | 0 |
| AS 89.3 | | 23 | −25 |
| AS 90.8 | | 23 | −31 |
| AS 93.3 | | 23 | −19 |
| AS 93.7 | | 23 | −6 |
| AS 96.5 | | 24 | 0 |
| AS 101.1 | | 24 | 0 |
| OH 192.3 | | 25 | −6 |
| OH 202.1 | | 25 | −8 |
| OH 202.3 | | 25 | 0 |
| OH 202.5 | | 25 | 0 |
| OH 202.6 | | 25 | 0 |
| OH 202.7 | | 16 | −13 |
| OH 202.9 | | 16 | −8 |
| OH 221.1 | | 26 | 49 |
| **OH 221.3** | | **16** | **8** |
| OH 232.1 | | 26 | 30 |
| OH 241.1 | | 26 | 49 |
| OH 241.2 | | 26 | 36 |
| OH 241.3 | | 26 | −13 |
| OH 241.5 | | 26 | 10 |
| OH 242.3 | | 26 | 18 |
| OH 242.4 | | 27 | 0 |
| OH 261.1 | | 27 | 0 |
| OH 262.1 | | 27 | 0 |
| OH 262.2 | | 27 | 0 |
| OH 262.3 | | 27 | −8 |
| OH 262.4 | | 27 | 0 |
| OH 262.5 | | 27 | −6 |
| OH 271.5 | | 16 | −17 |
| OH 271.5 | | 16 | −17 |

[a]Fully colonized liquid cultures (48 h) of microbial strains were diluted to one-quarter strength with a solution containing 0.004% phosphate buffer, 0.019% MgCl2 and 0.036% tween 80 and misted onto approximately 14 wheat heads at flowering (Feekes' growth stage 10.5.1). After 5 minutes, heads were then misted with a suspension of conidia of *Gibberella zeae* Z-3639 (5 × 105 coincubated in a humidity tent for 3 days, and scored for FHB disease development after 16 days.

[b]Best trial performance is presented if a strain was tested more than once.

[c]Negative or positive values represent % decrease or % increase in FHB severity, respectively, compared to the pathogen control (wheat heads treated with conidia of *Gibberella zeae*). Average FHB severity for control = 89%.

[d]Strain partially utilized choline in liquid culture bioassay.

[e]Field tested in 2002. Data not shown.

[f]Bold highlight = Strain selected for field trials in 2003.

TABLE 2

Choline-utilizing strain designator and identification of bacteria and yeast that reduce *Fusarium* head blight in wheat

| CUS designator[a] | Identification |
|---|---|
| AS 35.5 | *Erwinia* sp.[b,c] |
| AS 52.2 | *Pantoea agglomerans*[b,d] |
| AS 55.2 | *Aureobasidium pullulans*[e,f] |
| AS 64.4 | *Pseudomonas* sp.[b,g] |
| OH 221.3 | *Arthrobacter* sp.[b,h] |

[a]CUS = Choline-utilizing strain.

[b]Identification by MIDI Labs, Newark, DE, based on 16S rDNA 500 base-pair sequence homologies.

[c]Closest species match of *E. amylovora* differed from AS 35.5 by 1.52%

[d]Species match differed from AS 52.2 by 0.09%

[e]Identification by MIDI Labs, Newark, DE, based on the variable D2 region of the large sub-unit rDNA 300 base-pair sequence homologies.

[f]Species match differed from AS 55.2 by 0.31%

[g]Closest species matches of *Pseudomonas syringae*, *P. amygdali*, *P. savastanoi* and *P. fluorescens* F differed from AS 64.4 by 0.00%, 0.00%, 0.00% and 0.38%, respectively.

[h]Closest species match of *A. histidinolovorans* differed from OH 221.3 by 2.39%.

TABLE 3

Efficacy of choline-utilizing microbial strains against *Fusarium* head blight on wheat cultivars Freedom and P-2545 in a 2003 field test in Peoria, Illinois[a,b]

| Treatment[c] | DS (%) | DI (%) | 100-KW (g) |
|---|---|---|---|
| Freedom | | | |
| Untreated | 1.9# | 21# | 3.35 |
| Buffer/Tween | 0.9* | 11* | 3.29 |
| Folicur 3.6F | 1.1* | 12* | 3.32 |
| AS 35.5 | 0.8* | 7* | 3.34 |
| AS 52.2 | 1.1* | 9* | 3.27 |
| AS 55.2 | 1.0* | 10* | 3.28 |
| AS 64.4 | 0.7* | 8* | 3.26 |
| OH 221.3 | 0.9* | 7* | 3.28 |
| P-2545 | | | |
| Untreated | 4.0 | 32 | 3.13# |
| Buffer/Tween | 3.2 | 29 | 3.34* |
| Folicur 3.6F | 1.9*# | 20*# | 3.11# |
| AS 35.5 | 3.8 | 29 | 3.10# |
| AS 52.2 | 3.3 | 27 | 3.13# |
| AS 55.2 | 2.2* | 22*# | 3.21 |
| AS 64.4 | 2.6* | 19*# | 3.13# |
| OH 221.3 | 2.7* | 24* | 3.00# |

[a]DS = % Disease severity, DI = % Disease incidence, 100 KW = 100 kernel weight. Within a column, means followed by "*" and "#" are significantly different from the untreated check and buffer/tween check, respectively (FPLSD, P ≦ 0.05).

[b]Significant interactions complicate interpretation of pooled 100 KW data.

[c]Treatments were applied at 750 l/ha at the time of wheat flowering (Feekes' growth stage 10.5.1). Buffer/Tween consisted of a solution containing 0.004% phosphate buffer, 0.019% $MgCl_2$ and 0.036% Tween 80. Folicur 3.6F was applied at 292 ml/ha as per label instructions. Fully colonized microbial broths of antagonists were diluted 1:1 with Buffer/Tween before application.

TABLE 4

2003 Wooster, Ohio field test of the efficacy of choline-utilizing microbial strains against *Fusarium* head blight on wheat cultivars Freedom and P-2545[a,b]

| Treatment[c] | DS (%) | DI (%) | 100-KW (g) |
|---|---|---|---|
| Freedom | | | |
| Untreated | 26# | 93 | 2.36 |
| Buffer/Tween | 21* | 94 | 2.30 |
| Folicur 3.6F | 12*# | 80*# | 2.39 |
| AS 35.5 | 18* | 89 | 2.30 |
| AS 52.2 | 20* | 92 | 2.25 |
| AS 55.2 | 16*# | 89 | 2.30 |
| AS 64.4 | 14*# | 85*# | 2.32 |
| OH 221.3 | 16*# | 89 | 2.29 |
| P-2545 | | | |
| Untreated | 48 | 100 | 2.62 |
| Buffer/Tween | 50 | 100 | 2.50 |
| Folicur 3.6F | 42*# | 100 | 2.63 |
| AS 35.5 | 43*# | 100 | 2.54 |
| AS 52.2 | 46# | 99 | 2.49 |
| AS 55.2 | 41*# | 99 | 2.58 |
| AS 64.4 | 46# | 100 | 2.56 |
| OH 221.3 | 45# | 100 | 2.51 |

[a]DS = % Disease severity, DI = % Disease incidence, 100 KW = 100 kernel weight. Within a column, means followed by "*" and "#" are significantly different from the untreated check and buffer/tween check, respectively (FPLSD, P ≦ 0.05).

[b]Significant interactions complicate interpretation of pooled 100 KW data.

[c]Treatments were applied at 750 l/ha at the time of wheat flowering (Feekes' growth stage 10.5.1). Buffer/Tween consisted of a solution containing 0.004% phosphate buffer, 0.019% $MgCl_2$ and 0.036% Tween 80. Folicur 3.6F was applied at 292 ml/ha as per label instructions. Fully colonized microbial broths of antagonists were diluted 1:1 with Buffer/Tween before application.

We claim:

1. A biologically pure culture of a choline utilizing microorganism effective for control of *Fusarium* head blight in cereal plants, said microorganism being selected from the group consisting of *Aureobasidium pullulans* strain AS 55.2 (NRRL Y-50291), *Arthrobacter* species strain OH 221.3 (NRRL B-50290), and *Pseudomonas* species strain AS 64.4 (NRRL B-50289).

2. The biologically pure culture of claim 1, wherein said microorganism is said *Aureobasidium pullulans* strain AS 55.2 (NRRL Y-50291).

3. The biologically pure culture of claim 1, wherein said microorganism is said *Arthrobacter* species strain OH 221.3 (NRRL B-50290).

4. The biologically pure culture of claim 1, wherein said microorganism is said *Pseudomonas* species strain AS 64.4 (NRRL B-50289).

5. A method for suppressing *Fusarium* head blight in a cereal plant comprising applying to a head of said plant at least a first microbial antagonist selected from the group consisting of *Aureobasidium pullulans* strain AS 55.2 (NRRL Y-50291), *Arthrobacter* species strain OH 221.3 (NRRL B-50290), *Pseudomonas* species strain AS 64.4 (NRRL B-50289), and combinations thereof, said microbial antagonist being applied in an amount effective to reduce the level of *Fusarium* head blight relative to that in an untreated control.

6. The method of claim 5 wherein said microbial antagonist is applied to the head prior to hard dough stage of development.

7. The method of claim 5 wherein said microbial antagonist is applied to the head during flowering.

8. The method of claim 5 wherein said microbial antagonist is applied to the head prior to flowering.

9. The method of claim 5 wherein said cereal is wheat or barley.

10. The method of claim 9 wherein said cereal is wheat.

11. The method of claim 5, wherein said microbial antagonist is said *Aureobasidium pullulans* strain AS 55.2 (NRRL Y-50291).

12. The method of claim 5, wherein said microbial antagonist is said *Arthrobacter* species strain OH 221.3 (NRRL B-50290).

13. The method of claim 5, wherein said microbial antagonist is said *Pseudomonas* species strain AS 64.4 (NRRL B-50289).

14. The method of claim 5 wherein further comprising applying a second microbial antagonist effective for control of *Fusarium* head blight in cereal plants to said head.

15. The method of claim 14 wherein said second microbial antagonist is selected from the group consisting of *Bacillus* sp. (NRRL B-30210), *Bacillus* sp. (NRRL B-30211), *Cryptococcus aureus* (NRRL Y-30213), an unidentified yeast (NRRL Y-30214), *Bacillus* Sp. (NRRL B-30212), *Cryptococcus aureus* (NRRL Y-30215), and *Cryptococcus flavescens* (NRRL Y-30216).

16. The method of claim 15 wherein said second microbial antagonist is *Cryptococcus flavescens* (NRRL Y-30216).

17. The method of claim 15 wherein said first microbial antagonist and said second microbial antagonist are applied concurrently.

18. A composition for control of *Fusarium* head blight in cereal plants comprising a first and second microbial antagonists effective for control of *Fusarium* head blight in cereal plants, said first microbial antagonist selected from the group consisting of *Aureobasidium pullulans* strain AS 55.2 (NRRL Y-50291), *Arthrobacter* species strain OH 221.3 (NRRL B-50290), and *Pseudomonas* species strain AS 64.4 (NRRL B-50289).

19. The composition of claim 18 wherein said second microbial antagonist is selected from the group consisting of *Bacillus* sp. (NRRL B-30210), *Bacillus* sp. (NRRL B-30211), *Cryptococcus aureus* (NRRL Y-30213), an unidentified yeast (NRRL Y-30214), *Bacillus* sp. (NRRL B-30212), *Cryptococcus aureus* (NRRL Y-30215), and *Cryptococcus nodaensis* (NRRL Y-30216).

20. The composition of claim 19 wherein said second microbial antagonist is *Cryptococcus flavescens* (NRRL Y-30216).

* * * * *